United States Patent
Witham et al.

(10) Patent No.: US 7,107,778 B1
(45) Date of Patent: Sep. 19, 2006

(54) APPLIANCE FOR DISINFECTION OF HVAC SYSTEMS

(76) Inventors: David L. Witham, 2773 Seahorse Ave., Ventura, CA (US) 93001; Thomas M. Veloz, 27324 Bronco Dr., Canyon Country, CA (US) 91351; Thomas C. Bowles, 9091 Niguel Cir., Huntington Beach, CA (US) 92646; Roberto Arance, 25455 Via Dalla, Valencia, CA (US) 91355; Keith Crawford, 27226 Rockgrove Ave., Canyon Country, CA (US) 91351; Jon W. Orr, 1831 Marlowe St., Thousand Oaks, CA (US) 91360; Richard N. Metzger, 2257 Cooly Pl., Pasadena, CA (US) 91104; Larry F. Randall, 28465 N. Rock Canyon Pl., Santa Clarita, CA (US) 91350

( * ) Notice: Subject to any disclaimer, the term of this patent is extended or adjusted under 35 U.S.C. 154(b) by 1008 days.

(21) Appl. No.: 10/048,904

(22) PCT Filed: Sep. 15, 2000

(86) PCT No.: PCT/US00/25319

§ 371 (c)(1),
(2), (4) Date: Feb. 4, 2002

(87) PCT Pub. No.: WO01/30399

PCT Pub. Date: May 3, 2001

(51) Int. Cl.
*F25D 23/00* (2006.01)
*A62B 7/08* (2006.01)
*B01L 1/04* (2006.01)

(52) U.S. Cl. .................. 62/264; 422/121; 454/187

(58) Field of Classification Search .............. 62/264; 422/121; 454/187
See application file for complete search history.

(56) References Cited

U.S. PATENT DOCUMENTS

| 3,877,152 | A | * | 4/1975 | Gorman | 34/524 |
| 5,106,512 | A | | 4/1992 | Reidy | |
| 5,458,186 | A | | 10/1995 | Lee et al. | |
| 5,523,057 | A | * | 6/1996 | Mazzilli | 422/121 |
| 5,601,786 | A | | 2/1997 | Monagan | |
| 5,616,172 | A | * | 4/1997 | Tuckerman et al. | 96/16 |
| 5,664,340 | A | * | 9/1997 | Brown | 34/275 |
| 5,742,063 | A | * | 4/1998 | Scroggins et al. | 250/455.11 |
| 5,833,740 | A | | 11/1998 | Brais | |
| 5,837,207 | A | * | 11/1998 | Summers | 422/121 |
| 5,891,399 | A | | 4/1999 | Owesen | |
| 5,894,130 | A | * | 4/1999 | Bach | 250/436 |

(Continued)

FOREIGN PATENT DOCUMENTS

WO  WO 01/030399  5/2001

OTHER PUBLICATIONS

International Search Report of PCT Application No. US00/25319, Aug. 15, 2001, 4 pages.

*Primary Examiner*—William C. Doerrler
(74) *Attorney, Agent, or Firm*—Cislo & Thomas, LLP

(57) ABSTRACT

A device (20) for Disinfection of HVAC Systems that include features that will protect service personnel from un-intended exposure to ultra violet radiation. The safeguards include an interlock (70) that prevents illumination of germicidal lamps (80) when an enclosure within which the germicidal lamps (80) are mounted is not properly attached to a duct or appliance; the apparatus further provides for innovative methods for determining that the germicidal lamps (80) are operating.

2 Claims, 6 Drawing Sheets

U.S. PATENT DOCUMENTS 5,902,552 A * 5/1999 Brickley .................... 422/121
5,968,455 A    10/1999 Brickley
6,746,134 B1 * 6/2004 Guzorek .................... 362/647
6,809,326 B1 * 10/2004 Disabito et al. ........ 250/504 R

* cited by examiner

LAMP HANDLE ASSEMBLY

LAMP HANDLE/RETAINER ASSEMBLY

_US 7,107,778 B1_

APPLIANCE FOR DISINFECTION OF HVAC SYSTEMS

FIELD OF THE INVENTION

This invention relates to an appliance for use in the disinfection of heating ventilation and air conditioning systems ("HVAC"). More particularly, this invention relates to a device for killing microorganisms in both an air stream and/or stationary components within an HVAC system such as cooling coils, duct components and filter media, by irradiation with ultraviolet light ("UV"). The basic components of the system are an enclosure, removable UV lamp assemblies, a power supply to supply electrical power to the lamps, and various mechanical and electrical features to improve performance, convenience and safety.

More specifically, the present invention reduces the risk that those involved in installation and maintenance of HVAC equipment will be exposed to ultraviolet radiation when lamps are serviced or replaced, or when the unit is not properly positioned in a duct. Embodiments of the invention may also provide an indication of lamp operation visible from the outside of the duct to eliminate any need for direct visual observation of the lamps. An additional safety feature shuts off power to the lamps that produce ultraviolet radiation whenever a service person attempts to open the enclosure or remove the lamps to prevent exposure to harmful UV radiation. Other features of the invention provide improved performance and also ease of maintenance.

The inventive appliance is located within a self-contained unit that is installed in a portion of the duct work of an HVAC system or within a central HVAC appliance, such as a furnace, air conditioner or ventilating unit. The unit is generally mounted through an opening in the side of an HVAC duct. The electrical connections and ports are located on the outside of the duct, while the mercury vapor lamps that produce UV are located within the duct.

BACKGROUND OF THE INVENTION

Ultraviolet light in the range of wavelengths of from 180 to 300 nm has been used for the disinfection of air, water and surfaces for many years. Wavelengths near 253.7 nm are particularly useful for killing bacteria, viruses, fungus, mold and spores, and are conveniently generated by low pressure mercury vapor lamp. Many devices and methods for utilizing UV for disinfection are dislcosed in the prior art. Included in the prior art are devices for use in HVAC equipment for treatment of air streams and surfaces. However, these devices have not adequately addressed safety and performance issues.

"Disinfection" refers to killing pathogenic or otherwise undesireable micro-organisms. Products using short-wave ultraviolet radiation with wavelengths in the range of 180 to 350 nm have been used to disinfect air streams in residential and commercial HVAC systems. This is a high energy form of radiation that is not visible to humans. While this high energy ultraviolet light is capable of destroying a variety of biological pathogens and non-pathogenic, but nevertheless undesirable organisms, it is also hazardous to humans. Short wavelength ultraviolet radiation has been determined to be the cause of skin cancers, such as melanoma, and some cases of non-Hodgkins lymphoma by the National Center for Chronic Disease Prevention at the Centers for Disease Control and Prevention and by the National Cancer Institute. The eyes are particularly susceptible to damage caused by ultraviolet radiation. The upper threshold for exposure of the human eye to ultraviolet light has been set at 3 millijoules per square centimeter.

The lamps typically used to produce ultraviolet radiation for germicidal application produce a flux of ultraviolet radiation well in excess of this threshold, often 100 to 1000 times higher. Therefore, protective measures should be taken to protect workers and consumers who use ultraviolet light for germicidal applications.

Protective eyewear can adequately protect workers from health risk while working with ultraviolet devices. However, examination of Worker's Compensation Insurance claims reveal that one-half of the ultraviolet radiation related eye injuries occurred to workers who were in possession of, but neglected to use, proper protective eyewear.

In the past, sterilization and disinfection units were inadequately protected. While some units have electrical or mechanical mechanisms that may shut off a UV emitting germicidal lamp when it is removed from its enclosure, the device may be energized prior to installation, thereby subjecting the user or service person installing the unit to ultraviolet radiation.

Accordingly, an object of the invention to provide an appliance for disinfection of HVAC systems wherein only lamps that are optimized for the system can be mounted in the system;

It is a further object of the invention to provide an appliance for disinfection of HVAC systems designed to allow assessment of germicidal lamp performance without risk of exposure to ultraviolet radiation.

SUMMARY OF THE INVENTION

The present invention provides an integrated appliance for disinfection of HVAC systems that overcomes the deficiencies of prior art devices by providing a separate lamp assembly for each germicidal lamp. The invention may further provide that each lamp assembly can be separately removed from the appliance, and may further provide an optical signal for assessing performance of the lamp mounted in the lamp assembly. The invention may further provide novel switch assemblies that prevent application of electrical power when an enclosure containing the lamps is open for servicing, thus preventing exposure of service personnel to ultraviolet radiation.

DETAILED DESCRIPTION OF THE INVENTION

As shown in FIG. 1, in one embodiment, the appliance comprises an enclosure case (10) and a base (20). Base (20) is mounted to a wall of an HVAC duct (25). One or more openings are cut in the wall of the duct for the germicidal lamps (30) to project into the interior of the duct.

Base (20) includes a mechanical mount for one or more germicidal lamps, the electrical connections to the lamps, a power supply and ballast. The number of germicidal lamps (30) is determined by the intensity of the ultraviolet radiation required for the particular application. The germicidal lamps may be of a commercial design or specially made for this application. To insure the best match between lamp characteristics and the electrical properties of the power supply and ballast, in preferred embodiments germicidal lamps (30) are provided with specially designed mounts to engage lamp mounts on base (20) as described in greater detail below. The germicidal lamps may be configured as a single longitudinal tube (single or double ended), or a multi-axial tube.

Figure 2:
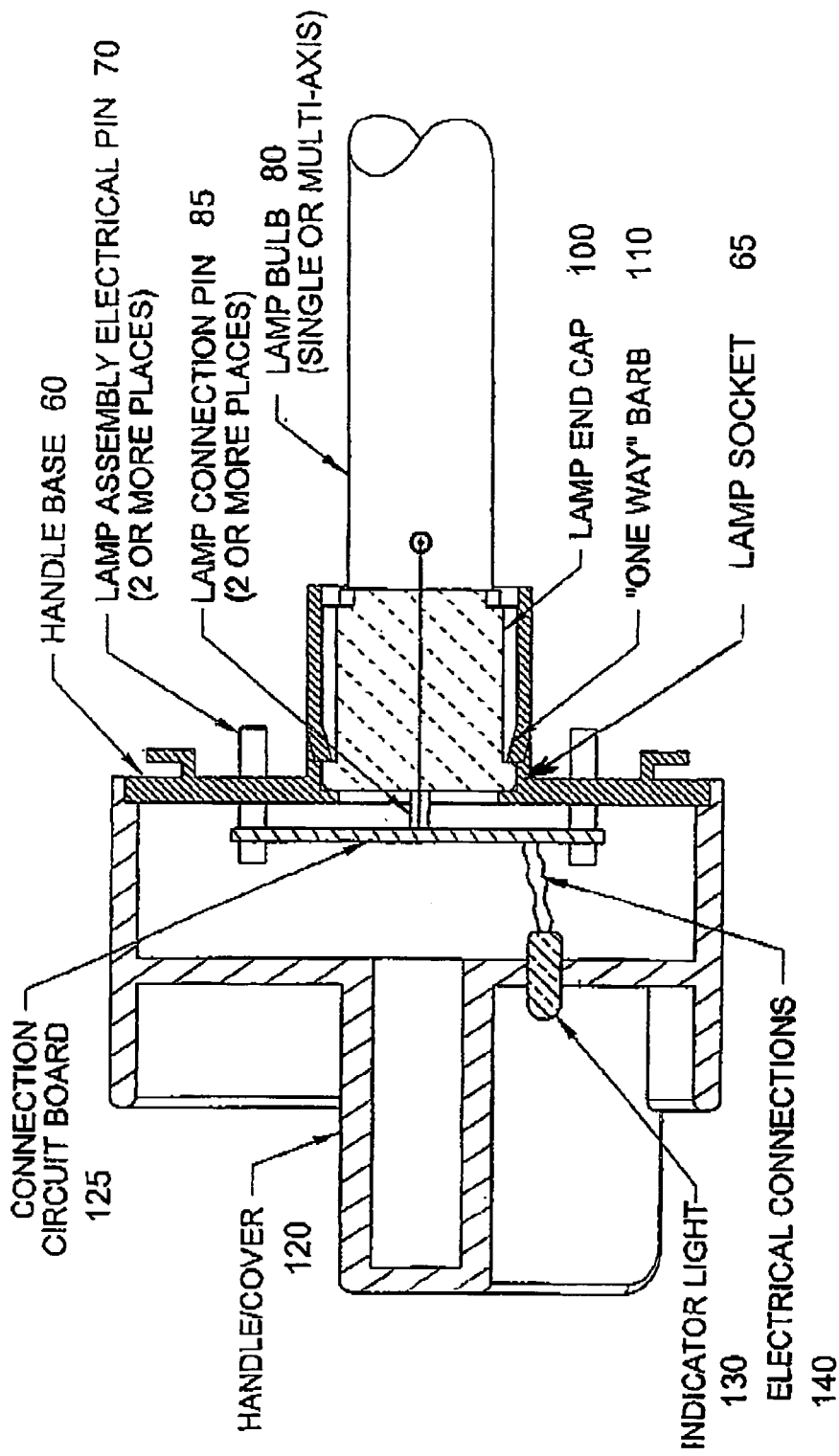
FIG. 2 is a cut-away side view.

The germicidal lamps are mounted in a specially designed socket described in greater detail below. As shown in FIG. 2 each lamp socket includes electrical connections to the lamp mounted therein. As also shown in FIG. 2 in preferred embodiments, lamp 65 socket is formed integral with handle base 60 to form lamp assembly 75 which is installed with the enclosure case 10. A section view of the lamp assembly is also shown in FIG. 2.

Figures 1A, 1B:
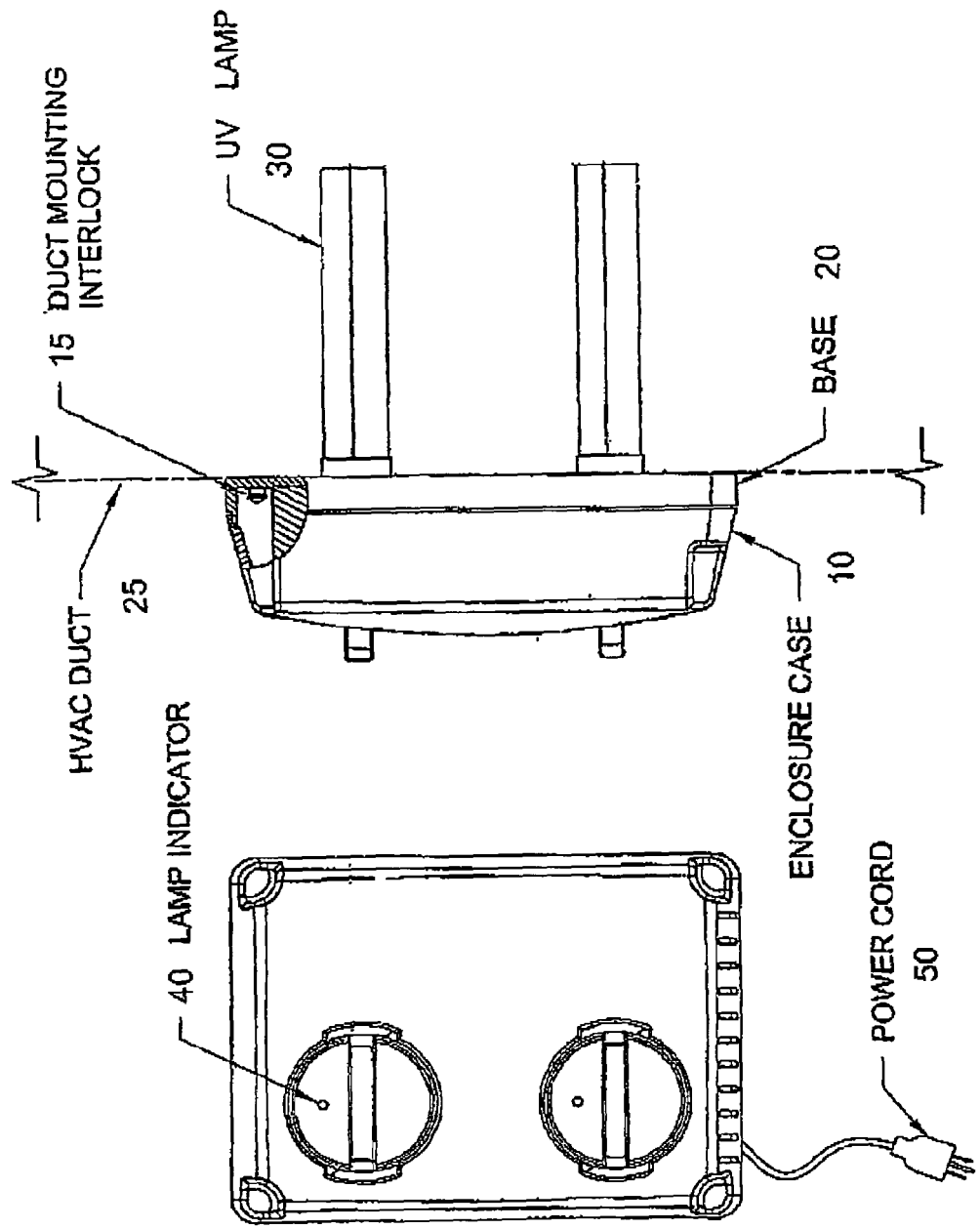
FIG. 1A is a front view of the device.
FIG. 1B is a side view of the device.
Figure 3:
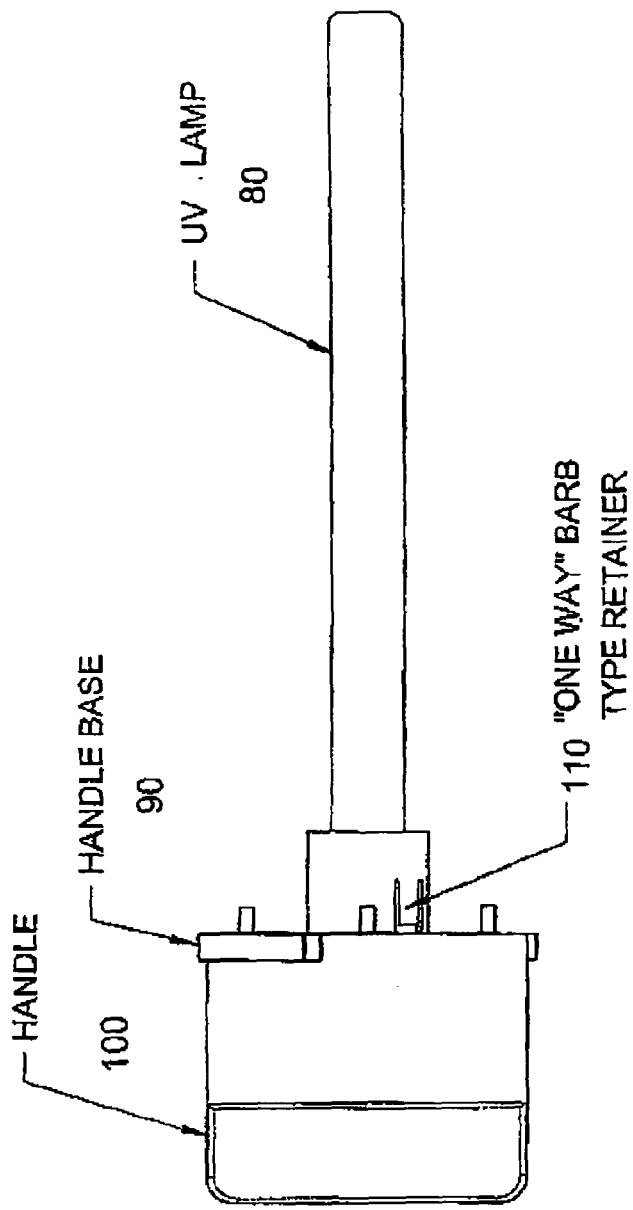
FIG. 3 shows the lamp handler/retainer assembly.

Each lamp is mounted separately in its own lamp assembly, allowing each lamp to be separately removed from service. As shown in FIG. 3 and in more detail in FIG. 5, the lamp assembly includes a handle base (60), a handle cover (120), a connection circuit board 125 and an indicator light (130), which, as discussed in greater detail below, provides an optical signal indicative of the state of operation of the lamp mounted on the particular lamp assembly. Lamp assembly 75 is attached to the enclosure case using a bayonet mount (not shown). A handle attached to the lamp assembly is grasped and rotated to release the lamp assembly from the enclosure case when it is necessary to service or replace the lamp. An end view of the enclosure case, with two lamp assembles is shown in FIG. 1A.

The invention further includes a duct mounting interlock (15) that prevents electrical power from reaching the ultraviolet lamps unless the enclosure is installed on an HVAC duct. Electrical power for the germicidal lamps is routed through a switch that is closed when a unit is attached to a duct or appliance. In preferred embodiments the switch is a paddle switch mounted on unit (20). When switch (15) is closed by attaching unit (20) to an HVAC duct or appliance, electrical current can reach the germicidal lamps.

In embodiments with provision for more than one lamp assembly in an enclosure, power will not be supplied to any lamp assemblies unless all lamp assemblies are installed. This aspect of the invention protects service personnel from exposure to UV radiation that would otherwise escape from the enclosure through unused openings for lamp assemblies. The presence of lamp assemblies may be detected by, for example, mechanical switches located adjacent to bayonet mounts for the lamp assemblies.

Figure 4A:
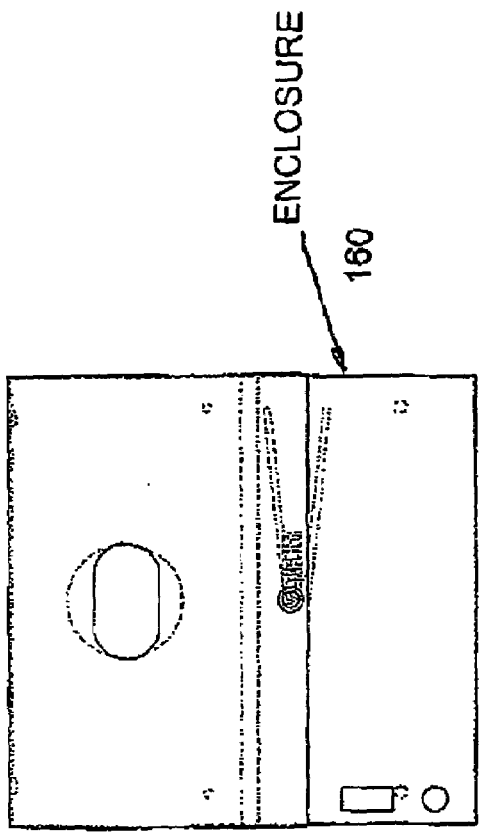
FIG. 4A is a front view showing the device mounted in a duct.
Figure 4B:
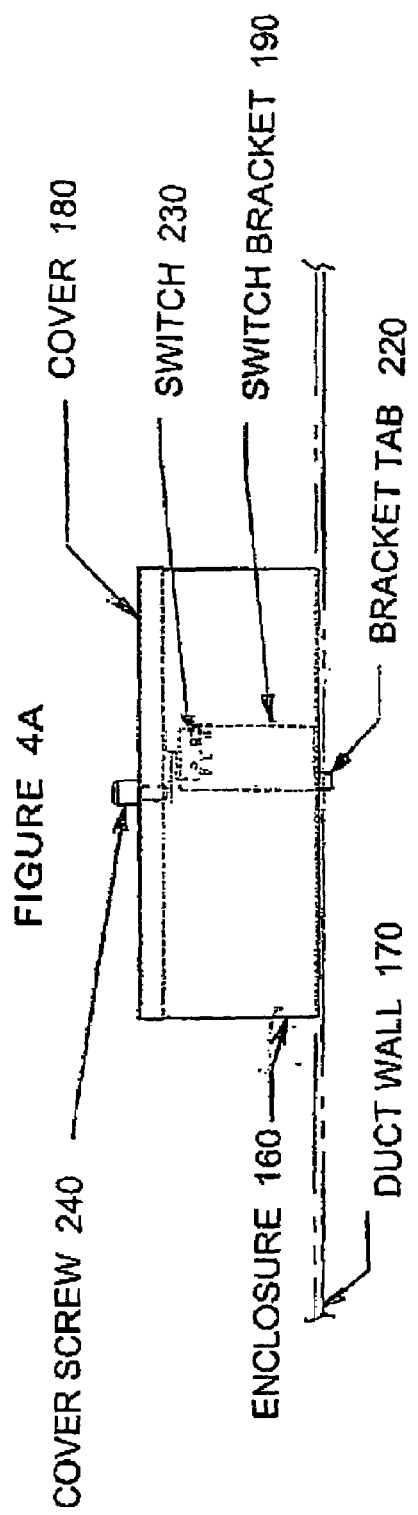
FIG. 4B is a side view showing the device mounted in a duct.
Figure 5:
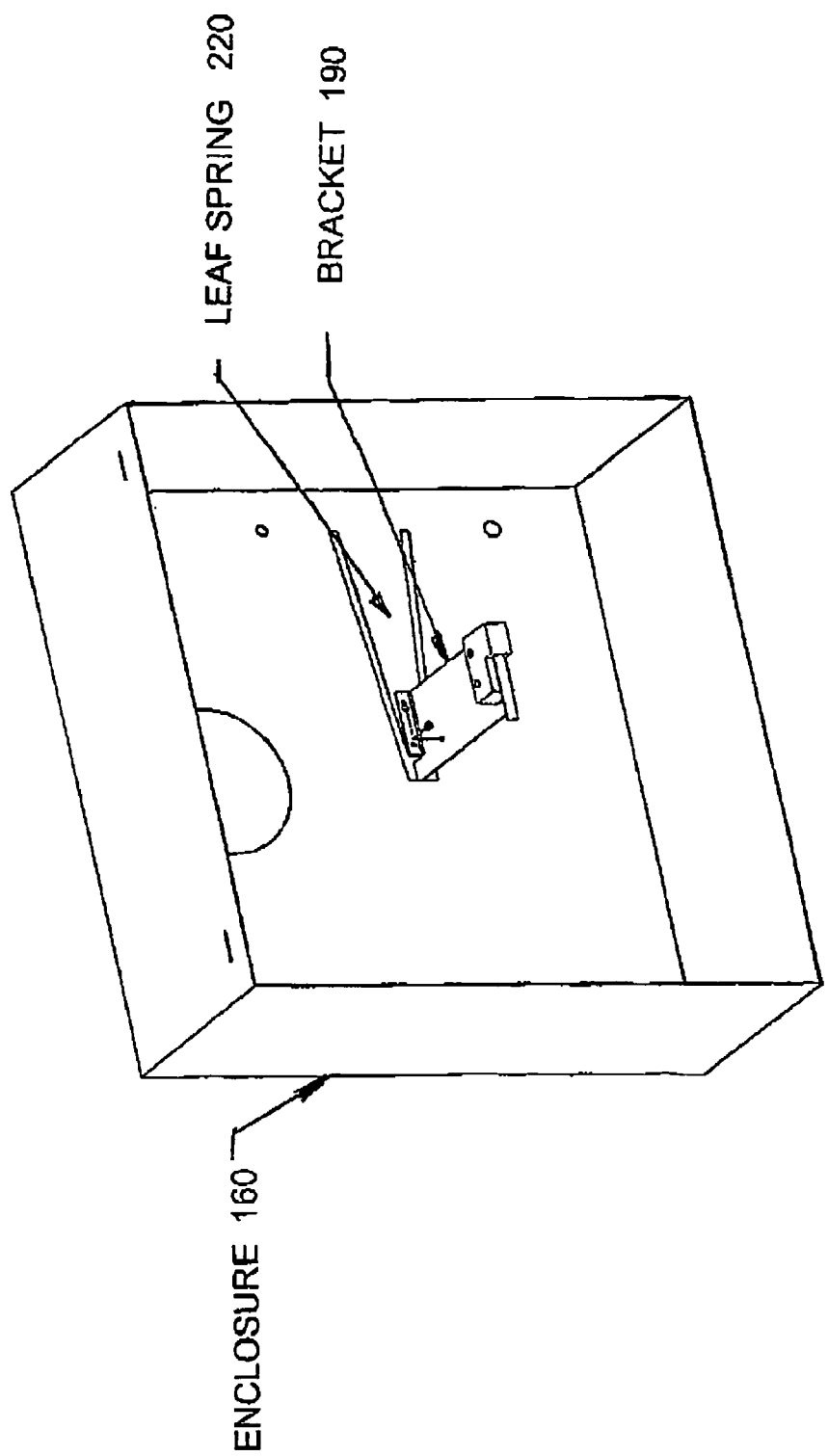
FIG. 5 shows the switch of the device.

Another embodiment of a device that prevents power from reaching the germicidal lamps unless the enclosure is installed in an HVAC duct or appliance is depicted in FIGS. 4 and 5. A side sectional view of this embodiment is shown in FIG. 4. In this embodiment, mounts for UV lamps are installed in a narrow box-shaped housing 160. In this embodiment, two conditions must be met before power is applied to the germicidal lamps. First, housing (160) must be mounted on the wall of a duct (170). Second, cover (180) must be attached to cover (180). Under these conditions, UV light will not be emitted unless the appliance of the present invention is attached to an HVAC duct, on one side, and that a cover is attached to the opposite side. Thus UV light should not be able to escape from the appliance.

Switch bracket (190) is mounted on a portion of the wall of housing (200) that is made flexible by cutouts made in wall forming a "v" shaped leaf spring (210). When housing (160, in FIG. 4) is mounted on duct wall (170) bracket tab (190) is deflected inward against spring pressure produced by leaf spring (220). As a consequence, switch bracket (190), which is attached to bracket tab (190) moves inward as well.

Interlock switch (230) is fixed to the end of switch bracket opposite the point at which switch bracket (190) is attached to leaf spring (210). Thus when switch bracket (190) is deflected inward, interlock switch (230) is carried forward as well. When interlock switch contacts cover screw (240) which is used to secure cover (250) in place, interlock switch (230) is defected backward, thus closing an electrical circuit that supplies power to germicidal lamps within the appliance. Thus, unless the appliance is mounted on an HVAC duct, pressing bracket tab (220) inward, and cover is attached to housing (160), power will not be applied to the germicidal lamps, and no UV will be produced. This mechanism will help to prevent inadvertent exposure to UV radiation produced by those who service and maintain the appliance.

Figure 6:
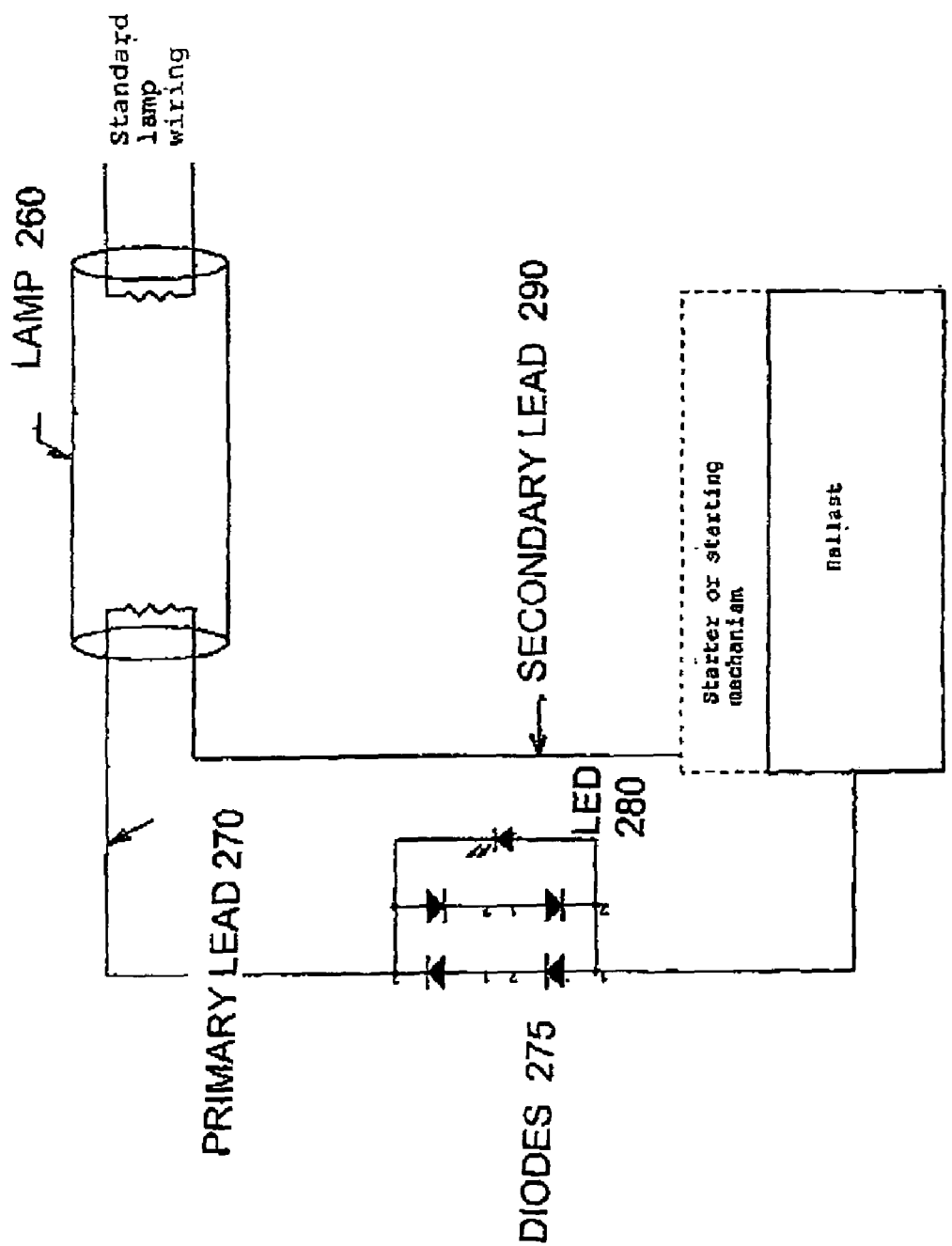
FIG. 6 is a circuit diagram for the device.

An additional safety feature of the invention is a visible indicator as to whether each lamp installed in a appliance according to the invention is illuminated. As shown in FIG. 6, AC power is supplied to the filaments of a low pressure mercury vapor germicidal lamp (260) through a pair of power circuits (270). Two pair of oppositely oriented diodes (275) are interposed in an arm of one power circuit (270). A light emitting diode ("LED") (280) illuminates when a voltage drop is present across the diode pair. The LED is only illuminated for a half cycle of the power wave form, but at frequencies of 60 Hz used in most installations, the off time is not detectable. Lamp failure is therefore readily detected, as the LED is not illuminated when there is no current flowing through the diodes.

The lamp base of the present invention is specifically implemented to prevent the installation of germicidal lamps not intended for use with the present invention. Although there are many sources for germicidal lamps, it is preferable to use lamps optimized for use with the inventive appliance disclosed and claimed herein. In some cases, lamps not designed for use with the present invention may not deliver the energy required by the particular installation.

Prior art appliances were designed to retain germicidal lamps in a variety of inefficient and costly designs. Some lamps were affixed to a base with a synthetic potting material. Others have used an awkward retaining device that may not prevent the installation of incorrect lamps. Other solutions provide a means to mount the germicidal lamp within the device, but are costly or difficult to manufacture. As shown in FIG. 2, the present invention employs a lamp base that engages protrusions formed on the lamp base with one-way barbs (110). This engagement mechanism securely fastens the germicidal lamp to the lamp base.

The foregoing description of the embodiments of the invention is provided for illustrative purposes and should not be understood to limit or otherwise to define the scope of the invention, which is provided by the claims appended hereinbelow.

We claim:

1. An apparatus for preventing operation of at least one germicidal lamp in an HVAC system under unsafe conditions comprising:
   a housing;
   a first switch on a side of the housing used to access the at least one germicidal lamp for servicing;
   a second switch on a side of the housing that is in contact with an HVAC duct or appliance,
   wherein power is supplied to the at least one germicidal lamp only when the first and second switches are in a condition indicating that the UV light cannot be emitted through the housing.

2. The apparatus of claim 1, wherein the first switch is a leaf switch.

* * * * *